United States Patent [19]

Lucas

[11] Patent Number: 5,122,119
[45] Date of Patent: Jun. 16, 1992

[54] HYPODERMIC SYRINGE

[76] Inventor: Dieter Lucas, Schlosstrasse 5, D-7763 Öhningen - Katternhorn, Fed. Rep. of Germany

[21] Appl. No.: 569,822

[22] Filed: Aug. 20, 1990

[30] Foreign Application Priority Data

Sep. 7, 1989 [DE] Fed. Rep. of Germany ....... 3929777

[51] Int. Cl.$^5$ ............................................. A61M 5/00
[52] U.S. Cl. .................................................. 604/135
[58] Field of Search ............... 604/134, 135, 136, 156, 604/157, 195, 198

[56] References Cited

U.S. PATENT DOCUMENTS

| | | | |
|---|---|---|---|
| 2,722,215 | 11/1955 | Dahlgren | 604/157 |
| 3,797,489 | 3/1974 | Sarnoff | 604/136 |
| 4,026,288 | 5/1977 | Costa et al. | 604/157 |
| 4,316,463 | 2/1982 | Schmitz et al. | 604/157 |
| 4,384,579 | 5/1983 | Lucas | 604/136 |
| 4,820,286 | 4/1989 | van der Wall | 604/134 |
| 4,850,967 | 7/1989 | Cosmai | 604/134 |
| 4,863,429 | 9/1989 | Baldwin | 604/135 |
| 4,894,055 | 1/1990 | Sudnak | 604/110 |
| 4,915,699 | 4/1990 | Kornberg | 604/195 |
| 4,978,343 | 12/1990 | Dysarz et al. | 604/110 |

Primary Examiner—Paul J. Hirsch
Attorney, Agent, or Firm—Bachman & LaPointe

[57] ABSTRACT

In a hypodermic syringe (10) with a hypodermic needle (20) which is adapted to be extended from a needle space (19) from a readiness position into an operative position by a force storage means (28), the invention seeks to make it possible to render the hypodermic needle (20) inaccessible after use. For that purpose the hypodermic needle (20) is arranged to be returned from the operative position by a force storage means (62) into the needle space (19) or a receiving space (11), which surrounds same at least at times, for receiving the needle space (19), or it is connected to a plunger (24) which is disposed in the needle space (19) and which is provided at its end face remote from the needle with at least one retaining recess for a pulling member, the recess being accessible from the exterior.

18 Claims, 3 Drawing Sheets

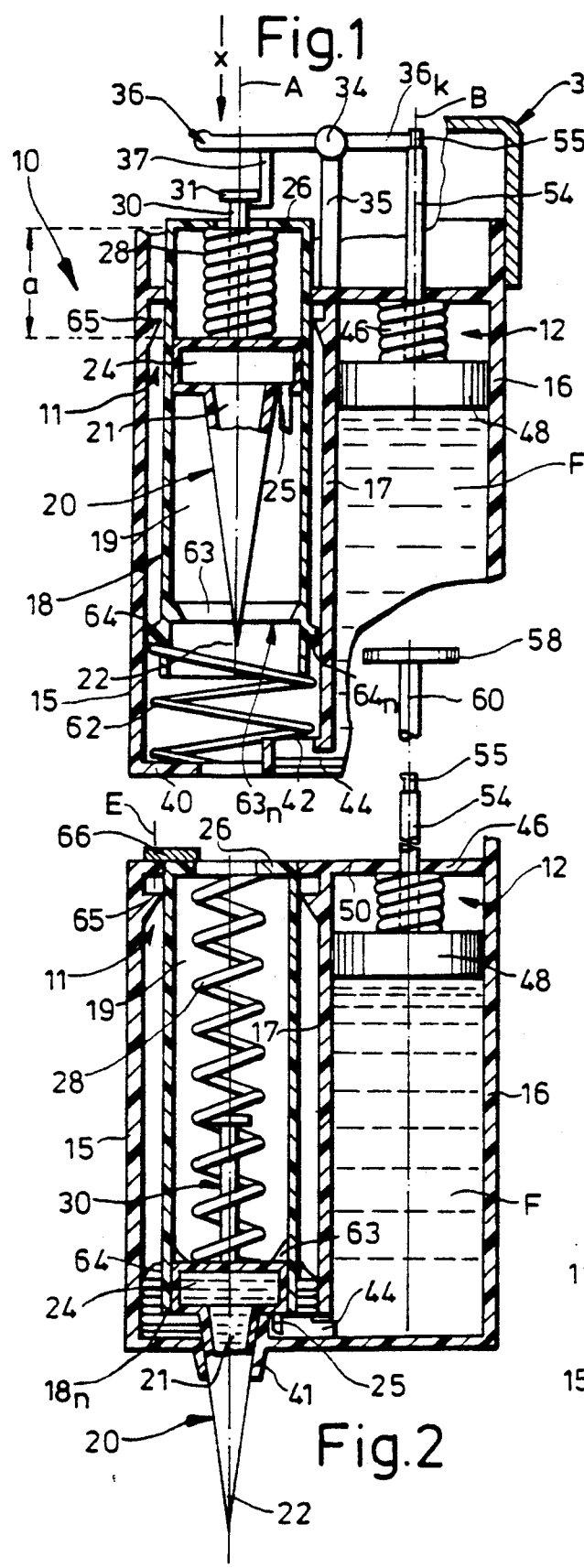
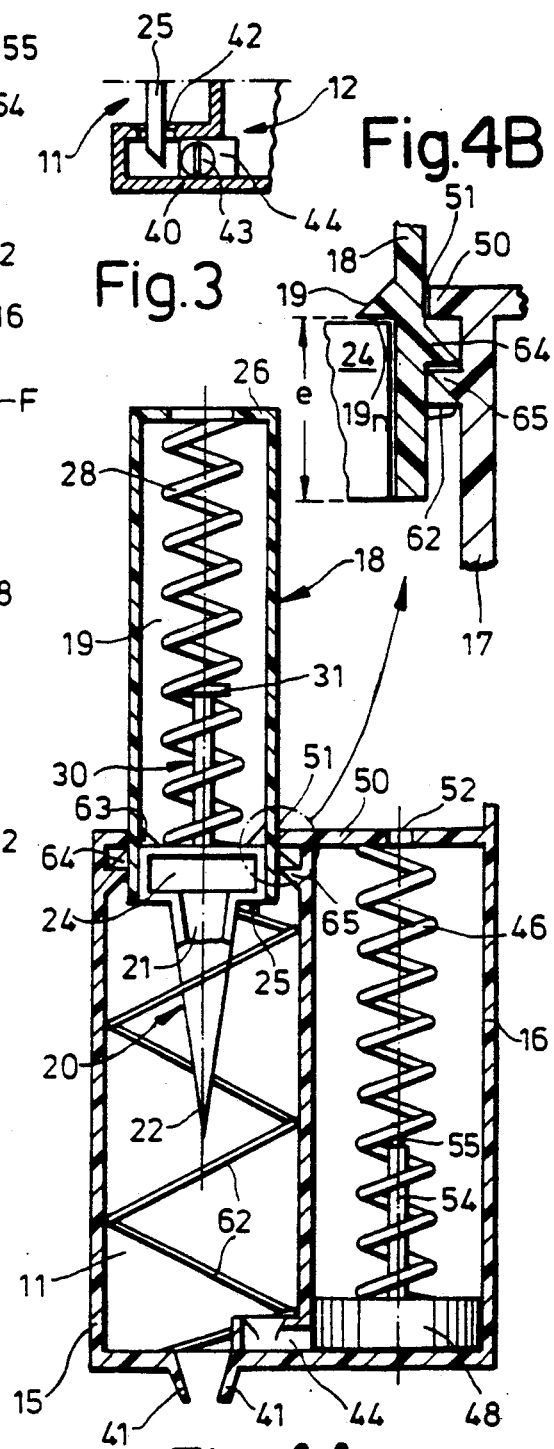

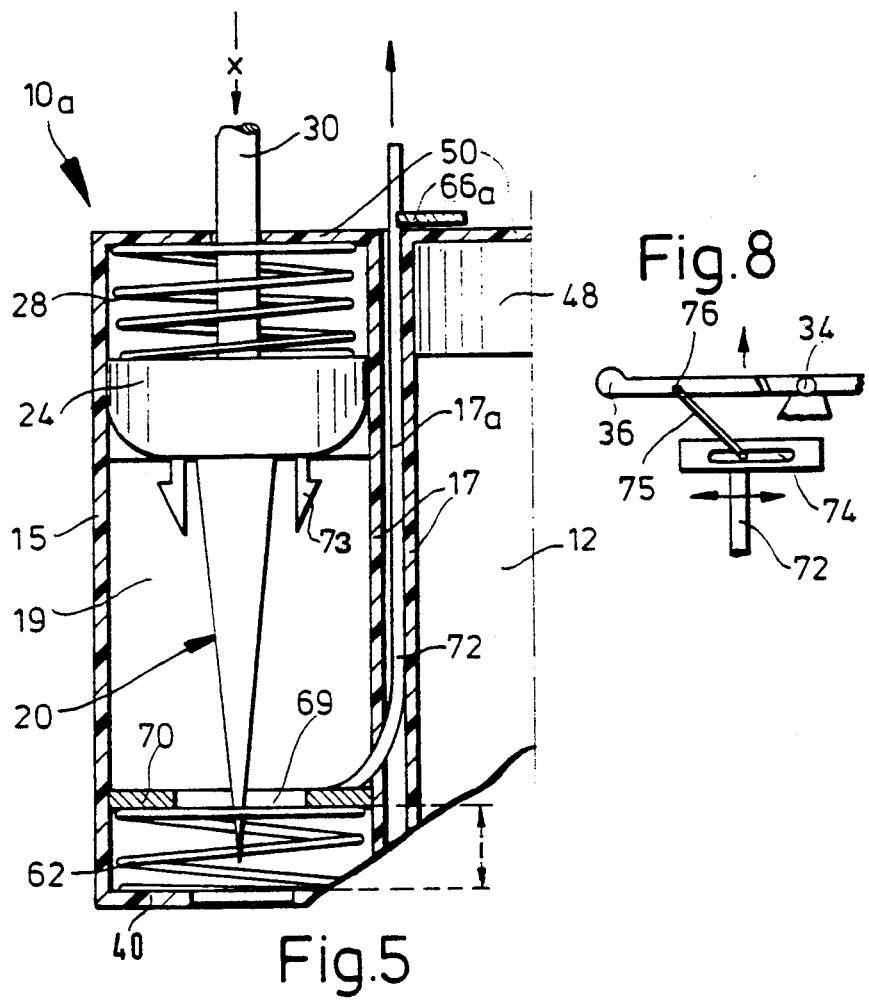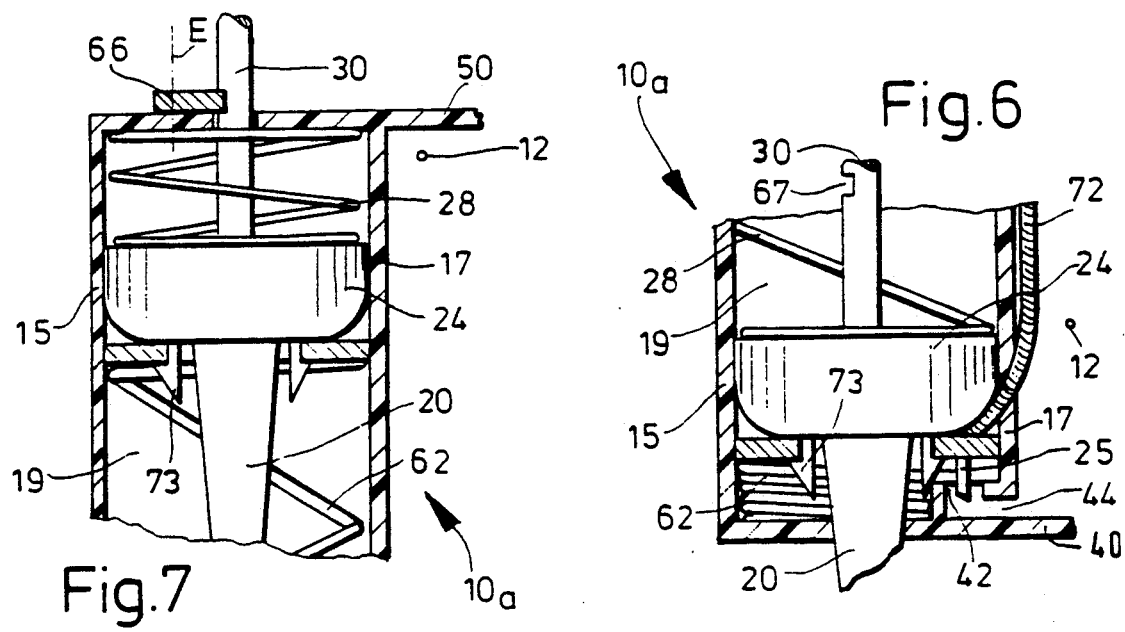

HYPODERMIC SYRINGE

BACKGROUND OF THE INVENTION

The invention relates to a hypodermic syringe comprising a hypodermic needle which can be extended from a needle space from a readiness position by a force storage means into an operative position. In particular the invention concerns a hypodermic syringe with a closed container which is arranged beside the needle space and which includes an injection material chamber and which receives a hypodermic liquid which can be put under pressure by a loadable pressure piston, wherein the hypodermic needle which has a needle duct is connected in the operative position to the injection material chamber.

Disposable syringes are known in which the needle must be screwed onto the syringe in order to put it into a condition in which it is capable of operation. The hypodermic liquid is taken from ampoules and is drawn up into the syringe. Manipulation with syringes of that kind is not satisfactory from the hygiene point of view, and is also time-consuming.

U.S. Pat. No. 4,556,100 discloses a syringe in which the hypodermic needle and the hypodermic liquid are disposed in a common space or chamber. The need is pushed out of the space under the pressure of a coil spring and at the same time the liquid is urged through a needle cannula. That arrangement suffers on the one hand from a disadvantage that the needle and the liquid are in constant contact with each other, in which case corrosion phenomena in respect of the needle due to the often corrosive liquids or impurities in the liquid cannot be excluded. In addition, in any case the liquid is also exposed with the needle so that it is not possible firstly to introduce the needle for example into the muscle tissue of a patient and then provide for delivery of the liquid.

The hypodermic syringe, in accordance with U.S. Pat. No. 4,384,579, was able to provide remedies in that respect.

SUMMARY OF THE INVENTION

The increasing concern about the consequence of injury to third parties by syringes which have already been used leads to the object of arranging for the needle thereof to be very substantially harmless after use thereof.

That object is achieved on the one hand in that the hypodermic needle is arranged to be returnable from the operative position by a force storage means into the needle space or a receiving space, which surrounds the needle space at least at times, for receiving the needle space. In addition the object envisaged by the inventor can also be attained in the hypodermic needle is connected to a plunger of the needle space and the latter is provided at its end face remote from the needle with at least one retaining recess which is accessible from the exterior, for a pull member. In the latter case the subject-matter of the invention is suitable in particular as a front attachment for pressure guns, as will be described in greater detail hereinafter.

In order to facilitate connection to such pressure attachments, the plunger of the hypodermic needle as well as the pressure piston of the injection material chamber are provided with the retaining recesses and the latter are preferably of the same configuration. In addition the hypodermic syringe is to be provided with fixing means for connection to counterpart elements of a pressure gun or the like; pressure members of the pressure gun are then associated with the plunger of the hypodermic needle and/or the pressure piston.

In a particular configuration of the hypodermic syringe, arranged axially movably between the plunger and the end or bottom of the needle space is a retaining member which is held in the readiness position against a force storage means which is supported towards the end or bottom and which is engaged by counterpart retaining means on the plunger when the hypodermic needle is moved into the operative position. It has been found to be desirable for the retaining member to be in the form of a ring or ring portion through which the hypodermic needle can pass and which is held by at least one releasable locking means in the readiness and operative position, against a spring. Engaging behind the ring as counterpart retaining means are flexible hook elements on the plunger which, when the latter is moved from the operative position into a closure position, entrain the ring, that is to say, the retaining member or the ring is urged upon release by the locking means, with the plunger bearing thereagainst, towards the closure plate of the needle space, by the force storage means. The locking means, preferably at least one locking bar which extends in axis-parallel relationship with respect to the hypodermic needle, can be connected with its free end to a substantially radially movable sliding linkage which liberates it abruptly when the injection operation is terminated and the hypodermic needle is to return into the casing.

Also in accordance with the invention is a hypodermic syringe in which the needle space for the hypodermic needle is provided in a sleeve which is axially movable in the receiving space. The sleeve is connected to a force storage means which can be stressed in the actuating direction. In that connection, in accordance with the invention, the hypodermic needle or the plunger thereof is held in the needle space by a spring which is then stressed, and the sleeve and the hypodermic needle hang on a stressing means, the sleeve and the injection needle being shot in a pressing direction upon release of the stressing means; in the operative position, in accordance with a further feature of the invention, the sleeve is locked in such a way that the hypodermic needle projects out of the receiving space.

The force storage means towards the bottom bears in the receiving space against an external lip or the like which extends on the sleeve adjacent the edge thereof which is towards the bottom or end of the syringe and, in the closure position, that is to say when the hypodermic needle is retracted or enclosed, it rests between the closure plate and an internal collar portion or the like of the receiving space.

The sleeve itself has an internal radial collar portion or the like internal lip, and the hypodermic needle engages under same in the operative position of the hypodermic syringe. By virtues of the provision of the radial collar portion, the plunger in the sleeve is held both in the operative position and also in the closure position in such a way that it forms a bottom portion for the sleeve. In accordance with the invention, the pairing of mutually facing radial members on the sleeve and the receiving space guarantees a firm positioning of the sleeve and therewith the hypodermic needle in the closure position of the syringe; in all the described constructions the hypodermic needle can be moved from the readiness position into the operative position in a simple manner and after use can be readily retracted into a casing portion to be inaccessible.

BRIEF DESCRIPTION OF THE DRAWINGS

Further advantages, features and details of the invention will be apparent from the following description of preferred embodiments and with reference to the drawings in which:

FIG. 1 shows a hypodermic syringe with two chambers which are disposed in parallel juxtaposed relationship, and a hypodermic needle, in a readiness position, FIG. 2 shows the hypodermic syringe of FIG. 1 in the operative position, FIG. 3 shows a detail from FIG. 2 on an enlarged scale, FIG. 4a shows the hypodermic syringe of FIGS. 1 and 2 in the emptied condition, 4b is an enlarged area of 4a, FIG. 5 shows a part of another hypodermic syringe in the readiness position, FIG. 6 shows the hypodermic syringe of FIG. 5 in the operative position, FIG. 7 shows the hypodermic syringe of FIGS. 5 and 6 in the emptied condition, FIG. 8 shows details of a specific closure means on the hypodermic syringe.

DETAILED DESCRIPTION

Figure 9:
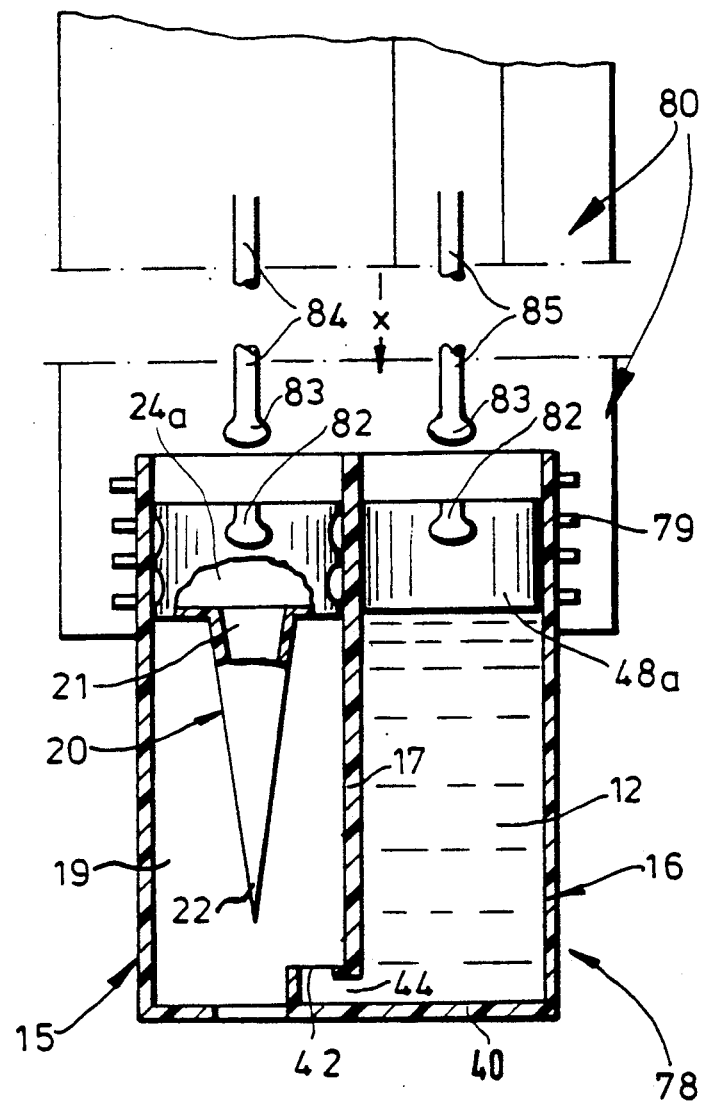
FIG. 9 shows a further hypodermic syringe in the readiness position.

The embodiment of a hypodermic syringe 10 for liquid medicaments, as shown in FIG. 1, comprises at least two cylindrical receiving spaces 11 and 12 in joined-together casings 15, 16 with parallel longitudinal axes A and B. A coaxial cylindrical sleeve 18 is axially displaceable in the receiving space 11 which is at the left in FIG. 1. A hollow needle 20 is disposed in the cylindrical sleeve 18 in the illustrated readiness position in such a way that the needle tip 22 thereof lies within the sleeve 18. In that arrangement, a hollow plunger 24 which carries the hollow needle 20 and which is guided in the needle space 19 of the sleeve 18 is disposed at a spacing a from a cover plate 26 of the sleeve 18, against which a coil spring 28 bears with its upper end. The lower end of the coil spring 28 applies a loading to the hollow plunger 24. Extending through the coil spring 28 is a plunger rod 30 with radially projecting plunger heat 31, which in FIG. 1 projects at the sleeve 18 and is held by an arresting means.

After the removal of a protective cap 32 which is jointly associated with the two casings 15 and 16, the plunger head 31 and therewith the plunger rod 30 are released by a pressure (arrow X) applied to a closure lever 36 which is pivotally connected at 34 to a pin 35; the hollow plunger 24 is moved downwardly towards the end or bottom 40 of the casing by the coil spring 28, in which case an eccentric needle connection portion 25 destroys a lateral sealing member 42 or the like in the receiving space 11 at the central wall 17; it closes off a passage chamber 44 provided with a valve ball member 43, with respect to the adjacent receiving space 42 which in the operative position as shown in FIG. 2 is communicated by way of the needle connection portion 25 to the hollow plunger 24 and thereby to the needle cavity 21. Liquid F at the receiving space 12 which serves as an injection material chamber immediately flows into the needle cavity 21 under the pressure of a pressure piston 48 which is loaded by a compression spring 46. The compression spring 46 is stressed in the readiness position of the hypodermic syringe 10 between the pressure piston 48 and a closure plate 50 which is common to the two casings 15 and 16. The closure plate 50 has apertures 51 and 52 therethrough, of different diameters, for the sleeve 18 on the one hand and for a guide rod 54 of the pressure piston 48 on the other hand. A hook head 55 on the guide rod 54 is held in the readiness position by the shorter lever arm $36_k$ of the closure lever 36 engaging thereunder; at the same time, the lever 36 secures the plunger head 31 by means of a downwardly projecting hook arm 37 on the longer lever arm $36_i$. Upon actuation of the lever 36 in the direction indicated by the arrow x, the plunger rod 30 and the guide rod 54, and therewith the coil springs 28 and 46, as already indicated above, are liberated, more specifically the guide rod 54 being liberated with a delay time relative to the downward movement of the plunger rod 30, so that the pressure or liquid piston 48 moves downwardly at a somewhat later time. That delay may be produced for example by sliding elements (not shown). In order to permit a slow movement of the pressure piston 48, the guide rod 54 thereof may also be provided with a handle 58 which in turn has a shank 60.

Moreover, when moving into the operative position shown in FIG. 2, the hypodermic needle 20 pierces the end or bottom 40 of the casing, the remains thereof bearing snugly against the side of the hypodermic needle 20, to constitute a sleeve portion 41.

The sleeve 18 is held in its upper readiness position by the fixed coil spring 28 and, upon the abrupt release of the coil spring 28, is driven downwardly with the hollow needle 20; when that happens, the hollow plunger 24 passes through a ring-like internal lip 63 of triangular cross-section and of flexible material, and engages behind the downwardly facing radial surface $63_n$ thereof. The spacing e thereof from the lower edge $18_n$ of the sleeve 18 corresponds to the height of the plunger.

A longer return spring 62 which is disposed in a prestressed condition between the bottom or end 40 of the casing and an external annular lip 64 on the sleeve 18 is further stressed when the sleeve 18 moves downwardly. The external lip 64 projects with its radial bottom surface $64_n$ from the sleeve 18, somewhat below the other bottom lip surface $19_n$.

During the injection procedure, a snap lock which is only indicated at 66 and which is pivoted about an axis E into the path of movement of the sleeve 18 holds the sleeve 18 in the operative position. When the snap lock 66 is released, the return spring 62 urges the sleeve 18 upwardly into a limit position as shown in FIGS. 4, in which the external lip 64 of the sleeve 18 moves beyond upper retaining ribs 65 on the casing 15; the lip 64 is clamped fast between the radial surfaces $65_h$, retaining ribs 65 and the closure plate 50 and the hypodermic needle 20 is thus fixed within the receiving space 11. That therefore prevents injury being caused by the hypodermic syringe 10.

In the embodiment shown in FIGS. 5 to 7 of a hypodermic syringe $10_a$, the hollow plunger 24 and the hypodermic needle 20 are held in the readiness position thereof by an arresting system (not shown) for the plunger rod 30. The upper coil spring 28 in this construction is disposed between the hollow plunger 24 and the closure plate 50 in the needle space 19 of the casing 15; this construction does not have a sleeve 18.

The return spring 62 is stressed between the bottom or end 40 of the casing and a pressure ring 70 which is held by a pressure lever 72 at a spacing i relative to the end or bottom 40 of the casing. The pressure lever 72 extends in a passage 17$_a$ in the central wall 17 and is actuable above the closure plate 50.

Projecting downwards from the hollow plunger 24 is a ring of limited flexible retaining hooks or claws 73 which, upon downward movement of the hollow plunger 24 (arrow x), pass through the central opening 69 in the pressure ring 70 and engage behind same with their hook heads; the hollow needle 20 is in the operative position (FIG. 6). The retaining hooks or claws 73 also ensure entrainment of the pressure ring 70 into the closure position of the hypodermic needle 20.

After use of the hypodermic syringe 10$_a$, the pressure levers 72 are released and the return spring 62 urges the hollow plunger 24 upwardly until, as shown in FIG. 7, its plunger rod 30 can be arrested by engagement of the snap lever 66 into a locking notch 67. Depending on its spring force, the return spring 62 is even sufficient to provide for secured fixing of the hypodermic needle 20 in the casing 15.

As shown in FIG. 8, the vertical pressure lever 72 may be provided with a sliding slot 74 which extends transversely with respect thereto and in which an inclined link member 75 can move radially with respect to the lever 72; at the other end the link member 75 is pivotally connected to the closure lever 36 at 76. When the closure lever 36 is raised the link member 75 is displaced and releases the pressure lever 72.

A syringe attachment 78 for a pressure gun 80 which is not shown herein for the sake of clarity of the drawing is screwed into the gun at 79. Provided in the plunger 24$_a$ and the piston 48$_a$, which are disposed slidably without a spring force in the needle space 19 and the receiving space 12 respectively are blind holes 82 of an undercut configuration, for heads 83, of a corresponding configuration, on actuating linkages 84, 85. The latter are shot in the direction indicated by the arrow x by the pressure gun 80, with a slight time delay.

After use the hollow needle 20 is retracted into the casing 15 by a pulling bar with head 83, which is inserted at 82.

I claim:

1. A hypodermic syringe comprising:
    a hypodermic needle having a needle duct therein, said needle having an operative position and a readiness position;
    a plunger connected to the needle;
    side by said first and second containers, said first container including a needle space therein with said needle disposed in the needle space in the readiness position, and said second container comprising a closed container arranged beside the needle space;
    a first force storage means acting on said plunger operative to extend the needle from the readiness position in the needle space to the operative position outside the needle space;
    an injection material chamber in the second container which accommodate a hypodermic liquid, wherein said chamber is connected to the needle duct in the operative position of the needle;
    a piston in the second container operative to put the hypodermic liquid under pressure;
    means to activate the piston in coordination with the activation of the plunger by the first force storage means;
    second force storage means for returning the hypodermic needle from the operative position to the needle space in a closure position, including means in the needle space engaging said second force storage means in the readiness position of the needle;
    means for retaining said needle in the operative position and releasing said needle from the operative position to permit return of the needle from the operative position to the closure position in the needle space by the second force storage means; and
    means for retaining the needle in the needle space int he closure position after return from the operative position by the second force storage means.

2. A hypodermic syringe according to claim 1 including fixing means for connection to counterpart elements of a pressure gun, and pressure members of the pressure gun associated with at least one of said plunger and piston.

3. A hypodermic syringe according to claim 1 wherein the plunger is spring loaded, and including a radial retaining member arranged axially movable between the spring-loaded plunger and the end of the needle space; said retaining member being held against the second force storage means in the readiness position, and including counterpart retaining means on the plunger engageable with the retaining member when the needle is moved into the operative position.

4. A hypodermic syringe according to claim 3 wherein the second force storage means is a spring, and wherein the retaining member includes a ring portion through which the needle can pass, including at least one releasable locking means operative to hold the retaining member against the second force storage means spring.

5. A hypodermic syringe according to claim 4 wherein the counterpart retaining means comprise flexible hook elements on the plunger which engage behind the ring portion in the pressure direction (x).

6. A hypodermic syringe according to claim 4 including a closure plate of the needle space, wherein the retaining member bears against the plunger in the operative position of the needle and upon release by the locking means is operative to move with the plunger towards the closure plate by the second force storage means.

7. A hypodermic needle according to claim 4 wherein the locking means comprises at least one locking bar which extends in axis-parallel relationship with respect to the needle and is held at the free end thereof by a substantially radially movable sliding linkage.

8. A hypodermic syringe according to claim 1 including an axially movable sleeve in the first container which surrounds the needle space, and including a receiver space in the first container with the second force storage means disposed in said receiving space, wherein the sleeve is connected to the second force storage means, and wherein said second force storage means can be stressed in the pressing direction (x).

9. A hypodermic syringe according to claim 8 wherein the first force storage means is disposed between the plunger and the sleeve and wherein the needle and the plunger are held in the sleeve in the readiness position of the needle by the first force storage means.

10. A hypodermic syringe according to claim 8 wherein the sleeve has a readiness position corresponding to the readiness position of the needle, and wherein the sleeve has an end adjacent the receiving space, and wherein the sleeve is held in its readiness position by the second force storage means at the sleeve end.

11. A hypodermic syringe according to claim 8 wherein the second force storage means is supported against an external lip on the sleeve.

12. A hypodermic syringe according to claim 10 including a closure plate of the needle space and an external lip on the sleeve adjacent the sleeve end, wherein said external lip in the closure position sits between the closure plate and an inwardly disposed retaining rib on the first container.

13. A hypodermic syringe according to claim 12 wherein the sleeve has an internal lip and the needle engages under the internal lip in the operative position of the needle.

14. A hypodermic syringe according to claim 13 wherein the internal lip and external lip are adjacent to each other on opposite sides of the wall of the sleeve.

15. A hypodermic syringe according to claim 8 wherein the sleeve is held in its readiness position in the first container adjacent the receiving space and wherein the plunger forms the base of the sleeve.

16. A hypodermic syringe according to claim 15 wherein the sleeve is locked in its readiness position against a spring force in the receiving space.

17. A hypodermic syringe comprising:

a hypodermic needle having a needle duct therein, said needle having an operative position and a readiness position;

a plunger connected to the needle;

side by side first and second containers, said first container including a needle space therein with said needle disposed in the needle space in the readiness position, and said second container comprising a closed container arranged beside the needle space;

a force storage means acting on said plunger operative to extend the needle from the readiness position in the needle space to the operative position outside the needle space;

an injection material chamber in the second container which accommodates a hypodermic liquid, wherein said chamber is connected to the needle duct in the operative position of the needle;

a piston in the second container operative to put the hypodermic liquid under pressure;

at least one retaining recess provided in each of the end faces of the plunger and piston remote from the needle which are accessible from the exterior, and corresponding pull members connected to said recesses, and linkages for actuating said pull members.

18. A hypodermic syringe according to claim 17 including fixing means for connection to counterpart elements of a pressure gun, and pressure members of the pressure sun associated with at least one of said plunger and piston.

* * * * *

UNITED STATES PATENT AND TRADEMARK OFFICE
CERTIFICATE OF CORRECTION

PATENT NO. : 5,122,119
DATED : June 16, 1992
INVENTOR(S) : DIETER LUCAS It is certified that error appears in the above-identified patent and that said Letters Patent is hereby corrected as shown below:

In Column 5, claim 1, line 64, "accommodate" should read --accommodates--.

In Column 6, claim 1, lines 16-17, "int he" should read --in the--.

In Column 6, claim 5, line 44, "pressure" should read --pressing--.

In Column 6, claim 8, lines 59-60, "receiver" should read --receiving--.

In Column 8, claim 18, line 30, "sun" should read --gun--.

Signed and Sealed this

Seventeenth Day of August, 1993

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,122,119
DATED : June 16, 1992
INVENTOR(S) : DIETER LUCAS It is certified that error appears in the above-identified patent and that said Letters Patent is hereby corrected as shown below:

Column 5, claim 1, line 52, "said" (first occurrence) should read

--side--

Signed and Sealed this

Eighth Day of February, 1994

Attest:

BRUCE LEHMAN

*Attesting Officer*   *Commissioner of Patents and Trademarks*